United States Patent [19]

Baker

[11] Patent Number: 5,007,911
[45] Date of Patent: Apr. 16, 1991

[54] DRILL HEAD ASSEMBLY FOR CRANIAL PERFORATORS

[76] Inventor: John W. Baker, 4 Wachusett Dr., Acton, Mass. 01720

[21] Appl. No.: 423,660

[22] Filed: Oct. 18, 1989

Related U.S. Application Data

[63] Continuation of Ser. No. 108,421, Oct. 14, 1987, abandoned.

[51] Int. Cl.⁵ .............................................. A61B 17/16
[52] U.S. Cl. ..................................... 606/80; 606/173; 408/139; 408/224
[58] Field of Search ................. 606/80, 172, 173, 180; 408/203, 201, 224, 225, 139, 703

[56] References Cited

U.S. PATENT DOCUMENTS

| 158,958 | 1/1875 | McCrosson | 408/224 |
| 252,704 | 1/1882 | Southwick | 408/224 |
| 2,525,669 | 10/1950 | Hainault | 408/703 X |
| 2,786,373 | 3/1957 | Patton | 128/310 |
| 4,600,006 | 7/1986 | Baker | 128/305.1 X |

Primary Examiner—Michael H. Thaler
Attorney, Agent, or Firm—Schiller, Pandiscio & Kusmer

[57] ABSTRACT

A drill head assembly for drilling holes in bony structure is disclosed. The assembly has an inner drill and an outer drill which rotate together as a unit. The leading portions of the outer drill are contiguous with the peripheral portions of the inner drill, and the inner and outer drills are adapted to form a bore-countersink opening in the bone, whereby the drill head assembly may be used to safely drill through relatively thin bone.

24 Claims, 4 Drawing Sheets

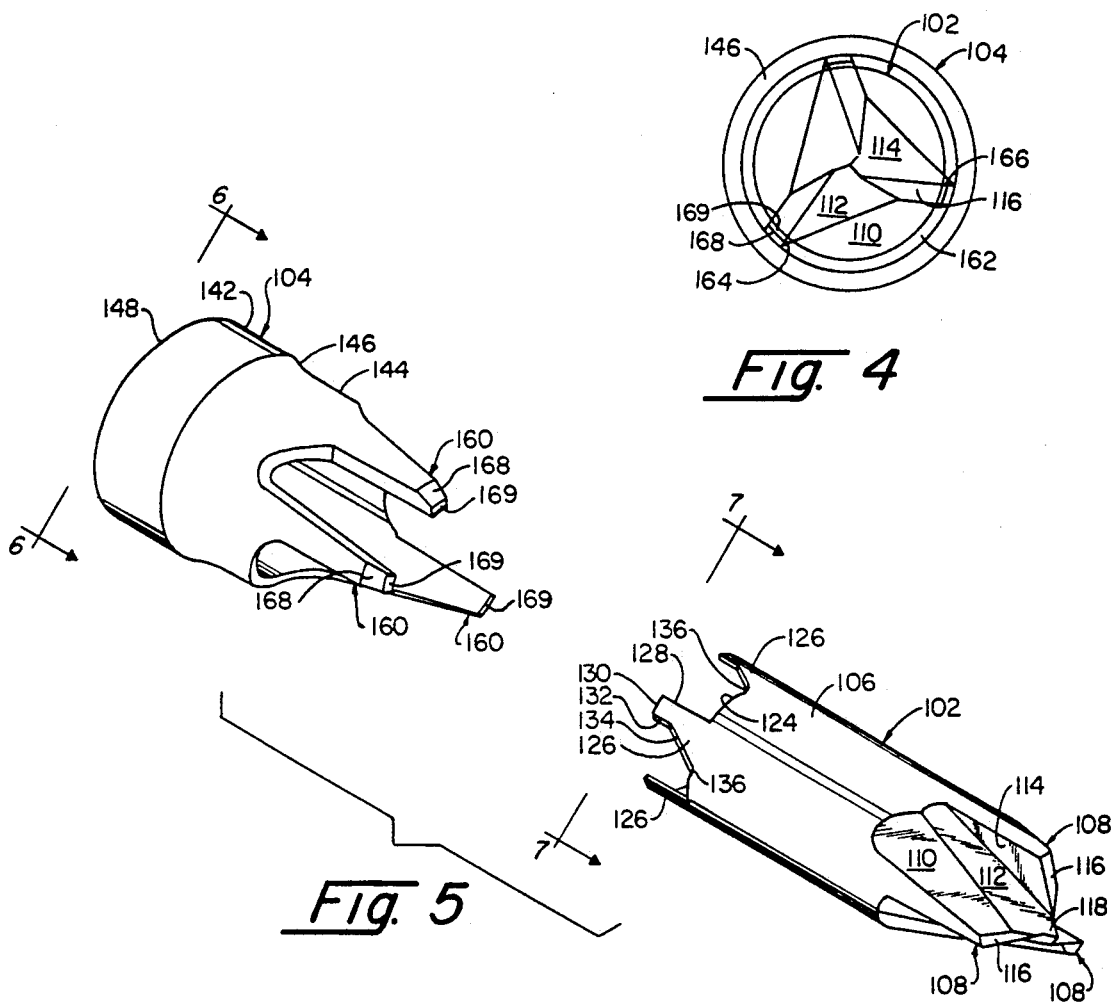
Fig. 4
Fig. 5
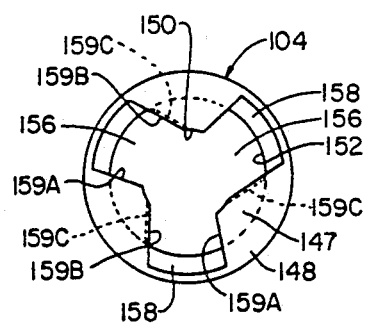
Fig. 6
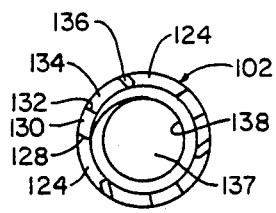
Fig. 7

DRILL HEAD ASSEMBLY FOR CRANIAL PERFORATORS

This is a continuation of U.S. patent application Ser. No. 108,421, filed on Oct. 14, 1987, now abandoned.

FIELD OF THE INVENTION

This invention relates to cranial perforators of the sort used to bore holes through the skull, and more particularly to the cutting surface configurations of such cranial perforators.

BACKGROUND OF THE INVENTION

Cranial perforators are special purpose drills which are used to bore holes through the skull during cranial surgery. Such holes may be needed to vent fluids from the region surrounding the brain, to provide small passageways to the brain for the insertion and removal of instruments, or to position a cranial saw for subsequent use in removing a larger piece of the skull.

Regardless of the end use of the hole being made, it is critical that the cranial perforator cease its boring action immediately after it passes through the skull and before it encounters, and thereby damages, the delicate dura tissue surrounding the brain, or the brain itself. To this end, cranial perforators have traditionally utilized a special "safety construction" designed to permit forward penetration by the perforator only so long as the perforator's leading tip is encountering hard bone, and to halt forward penetration by the perforator as soon as the perforator's leading tip passes through the hard bone and before it encounters the soft tissue beneath the bone. More particularly, cranial perforators have traditionally comprised a drill head assembly having a pair of drills disposed in concentric relation to one another, with the inner drill leading the outer drill so that a bore-counterbore opening is formed as the perforator penetrates into the skull. The two drills are coupled to a rear support and drive assembly via a special clutch arrangement such that both drills are enabled so long as the leading inner drill is encountering a resistive surface (i.e., bone) and both drills are disabled as soon as the inner drill stops encountering the resistive surface (i.e., as soon as it passes through the bone) while the outer drill is still encountering the resistive surface (i.e., while it is still cutting through the bone). Inasmuch as the leading inner drill and the trailing outer drill are adapted to cut in a bore-counterbore arrangement, the shoulder of bone formed at the intersection of the bore-counterbore opening automatically impedes further progress of the perforator toward the brain once the inner and outer drills are disabled. As a result, the surgeon using the cranial perforator does not have to concentrate entirely on the amount of pressure to be applied to the cranial perforator as the remaining bone becomes thinner and thinner, and generally need not fear that the perforator will penetrate too far into the head so as to damage the delicate dura tissue or the brain itself. Such cranial perforators have included both reusable and disposable models.

U.S. Pat. No. 4,600,006, issued July 15, 1986 to John W. Baker for "Cranial Perforator" discloses an improved form of cranial perforator incorporating the foregoing "safety construction". Other cranial perforators incorporating the foregoing "safety construction" are referenced in the specification of that patent or were cited in the prosecution of that patent. Still other cranial perforators incorporating the foregoing "safety construction" are disclosed in U.S. Pat. No. 4,803,982, issued Feb. 14, 1989 to John W. Baker for "Cranial Perforator".

Unfortunately, all of the "safety construction" cranial perforators developed to date are believed to suffer from a deficiency which can have catastrophic effects. This deficiency relates to the fact that all of the "safety construction" cranial perforators developed to date have their drill head assembly constructed so that the inner drill leads the outer drill and the inner and outer drills are adapted to cut in a bore-counterbore arrangement. Frequently, when drilling through very thin bone structures, the inner drill will pass all the way through the bone structure and into the delicate dura tissue, or even the brain, before the outer drill engages the bone structure, which engagement is necessary for the perforator's "safety construction" to impede further penetration of the perforator (i.e., by virtue of the fact that such engagement of the outer drill with the bone structure will (a) cause the inner and outer drills to be disengaged from the rear support and drive assembly and thereby drivingly disengaged, and (b) cause the outer drill, and hence the entire cranial perforator, to be supported on the shoulder of bone formed at the bore-counterbore opening in the skull). Thus, the perforator's "safety construction" becomes operative too late to prevent injury to the dura tissue or the brain. This situation occurs most often in pediatric drilling where the cranial bone is very thin, and in drilling in the thin rear temporal area of the skull in adults. Until now, a surgeon's skill and observations were his only tools to prevent penetration of the perforator into the dura or the brain in these cases.

OBJECTS OF THE PRESENT INVENTION

Accordingly, the primary object of the present invention is to provide an improved drill head assembly for "safety construction" cranial perforators which eliminates the aforementioned problem related to drilling through very thin bone structures.

Another object of the present invention is to provide an improved drill head assembly for "safety construction" cranial perforators which is designed so that the outer drill will contact hard bone at substantially the same time that the peripheral edges of the inner drill start cutting into the bone.

And another object of the present invention is to provide an improved drill head assembly for "safety construction" cranial perforators which will yield a stronger shoulder of bone to impede further progress of the perforator toward the brain once the inner and outer drills are disengaged.

And another object of the present invention is to provide an improved drill head assembly which can be used with cranial perforators of the sort disclosed in U.S. Pat. No. 4,600,006 (Baker) and U.S. Pat. No. 4,803,982 (Baker), as well as with other "safety construction" cranial perforators.

SUMMARY OF THE INVENTION

These and other objects of the present invention are achieved through an improved drill head assembly comprising inner and outer drills disposed in concentric relation to one another, wherein the leading edges of the outer drill are disposed substantially even with the peripheral edges of the inner drill, and the inner and outer drills are adapted to cut in a bore-countersink arrangement as the perforator penetrates into the skull.

On account of the foregoing construction, when the improved drill head assembly is mounted to a rear support and drive assembly via a suitable clutch arrangement so that both drills are enabled so long as the inner drill is encountering a resistive surface (i.e., bone) and both drills are disabled as soon as the inner drill stops encountering a resistive surface (i.e., as soon as it passes through the bone) while the outer drill is still encountering the resistive surface (i.e., while it is still cutting through the bone), the leading edges of the outer drill will engage the bone at substantially the same time that the peripheral edges of the inner drill engage the bone, and a shoulder of bone will always be present beneath the outer drill to impede further progress of the perforator toward the brain once the inner and outer drills are disabled.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIG. 4 is an end view of the drill head assembly shown in FIG. 2;

FIG. 5 is an exploded perspective view of the drill head assembly shown in FIG. 2;

FIG. 6 is a rear elevation of the outer drill of the same drill head assembly, taken from the viewpoint represented by line 6—6 in FIG. 4;

FIG. 7 is a rear elevation of the inner drill of the same drill head assembly, taken from the viewpoint represented by line 7—7 in FIG. 4;

DETAILED DESCRIPTION OF THE DRAWINGS

Figure 1:
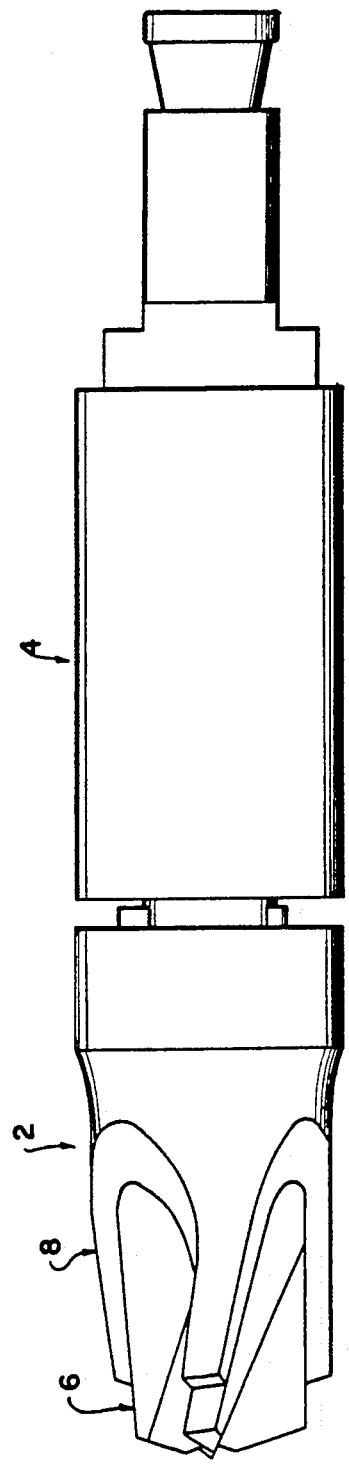
FIG. 1 is a side elevation of a prior art cranial perforator.
Figure 3:
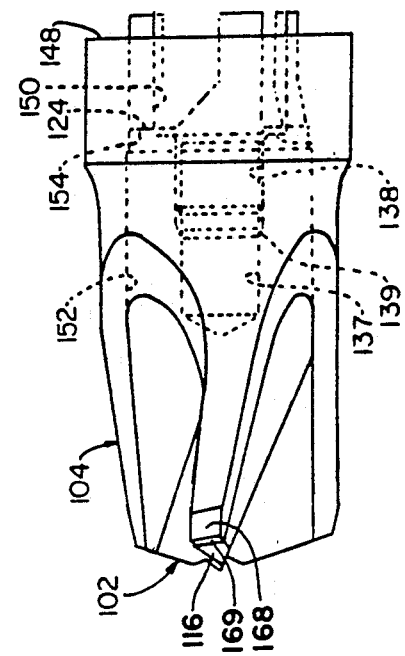
FIG. 3 is a side elevation of the drill head assembly shown in FIG. 2, the drill head assembly being rotated 60 degrees from the position shown in FIG. 2 and certain internal parts being shown in phantom.

Looking first at FIG. 1, there is shown a prior art cranial perforator of the type disclosed in U.S. Pat. No. 4,600,006 (Baker). The cranial perforator generally comprises a front drill head assembly 2 and a rear support and drive assembly 4. Front drill head assembly 2 generally comprises an inner drill 6 and an outer drill 8. Details on the construction and function of front drill head assembly 2 and rear support and drive assembly 4 are provided in U.S. Pat. No. 4,600,006 (Baker), which is incorporated herein by reference. It is important to note that with the prior art front drill head assembly 2 shown in FIG. 1, the leading edges of the outer drill 8 are spaced significantly back from the peripheral edges of the inner drill 6, and the inner and outer drills are arranged so as to cut a bore-counterbore opening in the bone.

Figure 2:
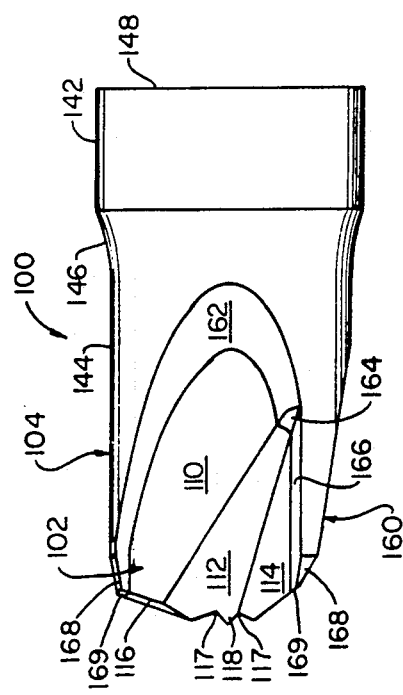
FIG. 2 is a side elevation of a drill head assembly which comprises one embodiment of the present invention, the drill head assembly being rotated 60 degrees from the position shown with respect to the prior art device shown in FIG. 1.

Looking next at FIG. 2, the present invention provides an improved front drill head assembly 100 which is intended to replace the front drill head assembly 2 shown in FIG. 1.

Front drill head assembly 100 comprises an inner drill 102 and an outer drill 104.

Inner drill 102 is shown in FIGS. 2-5, 7 and 8. Drill 102 is generally cylindrical in nature and comprises a cylindrical midsection 106 (FIG. 5). The front end of drill 102 is dissected by a plurality of inclined intersecting surfaces so as to define three prismatic flutes or blades identified generally at 108. More particularly, the three flutes 108 comprise a trio of first inclined surfaces 110, a trio of second inclined surfaces 112, and a trio of third inclined surfaces 114, plus a trio of end surfaces 116, with each of the latter being intersected by one of the surfaces 110, 112 and 114.

Flutes 108 are disposed 120 degrees apart from one another. Accordingly, each of the surfaces 110, 112 and 114 of a given flute is displaced 120 degrees from its corresponding surface on the other two flutes. On account of the relative dispositions of the inclined surfaces 110, 112, and 114, each of the flutes 108 includes a front end notch 117 (FIGS. 2 and 3), and the inner drill terminates in a pyramidal front end projection 118 which extends outward beyond the front end surfaces 116 of flutes 108 (FIGS. 2 and 5). The planes of surfaces 114 are eccentric to the lead point of pyramidal end projection 118 (see FIGS. 4 and 5), and end surfaces 116 extend at a 17 degree angle in the radial direction (see FIG. 8) and are pitched at a 6 ½ degree angle in the circumferential (i.e., non-radial) direction (see FIG. 4). The front leading edges of surfaces 116 constitute front cutting edges and the outer edges of surfaces 114 constitute side cutting edges.

The rear end of cylindrical midsection 106 terminates in an end surface or wall 124 (FIGS. 4 and 7). A trio of lugs or keys or fingers 126 extend rearward from end surface 124. Rearwardly projecting lugs 126 are formed integral with cylindrical midsection 106 and are disposed 120 degrees apart from one another. Each of the lugs 126 is shaped so that it has a first side surface 128 which extends parallel to the center axis of drill 102 and perpendicular to end surface 124, an end surface 130 which extends substantially parallel to end surface 124, a second side surface 132 which extends substantially perpendicular to end surface 124 and end surface 130, and a third side surface 134 which extends at an inclined angle (i.e., non-perpendicular) to end surface 124, as disclosed in U.S. Pat. No. 4,600,006 (Baker). Alternatively, third side surface 134 may be helically twisted in the manner disclosed in U.S. Pat. No. 4,803,982 (Baker). A small groove 136 is formed at the intersection of each inclined side surface 134 and end surface 124.

Inner drill 102 also includes an axial bore 137 (see FIG. 3) which begins at rear end surface 124 of cylindrical midsection 106 and terminates in the middle of midsection 106, and a threaded counterbore 138 which begins at rear end surface 124 of cylindrical midsection 106 and terminates at a shoulder 139 in the middle of midsection 106. Axial bore 137 and threaded counterbore 138 are adapted to receive a portion of the rear support and drive assembly 4 shown in FIG. 1, in the manner disclosed in U.S. Pat. No. 4,600,006, whereby front drill head assembly 100 may be attached to the rear support and drive assembly 4. Alternatively, axial bore 137 and threaded counterbore 138 may receive corresponding parts from other types of known rear support and drive assemblies, so that front drill head assembly 100 may be attached to and utilized with such support and drive assemblies.

Outer drill 104 is shown in FIGS. 2-6 and 8. Outer drill 104 is generally cylindrical in nature, and is cut away in a selected manner so as to form a series of flutes or blades at its front end. More particularly, outer drill 104 comprises a substantially cylindrical rear section 142 which is joined to a generally cylindrical front section 144 by a substantially frustoconical section 146 (FIGS. 2 and 5). Rear section 142 terminates in a rear surface 148 (FIGS. 2, 5 and 6). Outer drill 104 includes an axial bore 152 (FIG. 6), and three inwardly extending lips or dogs 147 having forward surfaces 154 (FIG. 3) and curved inside surfaces 150 which are arcs of a circle concentric to the axis of the outer drill. Outer drill 104 also includes a trio of slots 156 extending between lips 147. Slots 156 are spaced 120 degrees apart from one another. Each of the slots 156 forms a shoulder 158. Each of the lips 147 has side wall surfaces 159A and 159B. Lips 147 are bevelled away at their forward sides so that surfaces 159C extend between side wall surfaces 159B and forward surfaces 154. Surfaces 159C are planar in nature and extend at a 45 degree angle to side wall surfaces 159B and at a 45 degree angle to forward surfaces 154, for reasons which are made clear in U.S. Pat. No. 4,600,006 (Baker).

Referring next to FIGS. 2, 4 and 5, the outer drill's generally cylindrical front section 144 is dissected by a plurality of inclined intersecting surfaces so as to define three flutes or blades identified generally at 160. More particularly, the three flutes comprise a trio of first inclined surfaces 162, a trio of second inclined surfaces 164, and a trio of third inclined surfaces 166.

Figure 8:
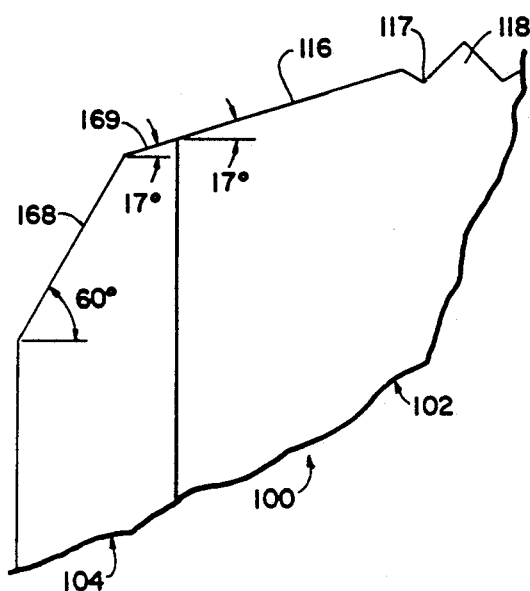
FIG. 8 is an enlarged partial side elevation of the drill head assembly shown in FIG. 2.

Flutes 160 are disposed 120 degrees apart from one another, and each terminates in front end surfaces 168 and 169 (see FIGS. 2, 5 and 8). Front end surfaces 169 extend at a 17 degree angle to a plane that intersects the axis of the drill head assembly at a right angle (see FIG. 8), and front end surfaces 168 extend at a 60 degree angle to a plane that intersects the axis of the drill head assembly at a right angle (see FIG. 8). Front end surface 160 preferably extends for 15/1000 inch in the radial direction, although it could extend for a shorter (e.g. 5/1000 inch) or a longer (e.g. 30/1000 inch) distance in practice. Surfaces 168 and 169 are formed from a frustoconical section pitched at a 3 degree angle in the circumferential (i.e., non-radial) direction (see FIG. 4). The leading edges of surfaces 168 and 169 are front cutting edges, while the outer edges of surfaces 166 constitute side cutting edges.

Inner drill 102 and outer drill 104 are assembled concentrically one inside the other so as to form the complete drill head assembly 100. More particularly, inner drill 102 and outer drill 104 are positioned in the manner shown in FIG. 5, i.e., so that the inner drill's flutes 108 are aligned with the outer drill's flutes 160, and so that the inner drill's lugs 126 are aligned with the outer drill's slots 156. Then the two drill members are brought together, so that the inner drill slips inside and makes a close sliding fit with the outer drill, with the inner drill's end wall 124 coming to rest against the forward surfaces 154 of lips 147. The various parts of the inner and outer drills are sized and shaped so that when the drill head assembly is put together with the inner drill's end surface 124 engaging the outer drill's surfaces 154, and the lugs 126 are located in slots 156, the outer drill's front end cutting surfaces 168 and 169 will be radially aligned with and form a rearward extension of the inner drill's front end surfaces 116, the leading portions of the outer drill's front cutting surfaces 169 will be contiguous with the peripheral portions of the inner drill's leading surfaces 116 (see FIG. 8), the outer drill's first inclined surfaces 162 will form a rearward extension of the inner drill's first inclined surfaces 110, the outer drill's second inclined surfaces 164 will form a rearward extension of the inner drill's second inclined surfaces 112, and the outer drill's third inclined surfaces 166 will form a rearward extension of the inner drill's third inclined surfaces 114 (see FIGS. 2 and 4). In addition, the inner drill's lugs 126 are sized so that when the inner drill's end wall 124 engages the outer drill's surfaces 154, the lugs 126 extend out through the outer drill's slots 156, with the lugs' first side surfaces 128 residing adjacent and parallel to side surfaces 159A of lips 147, and the lugs' inclined side surfaces 134 residing adjacent and parallel to bevelled surfaces 159C of lips 147. In addition, the inner drill's lugs 126 are sized so that they extend out beyond the outer drill's rear surface 148 when the inner drill's end wall 124 engages surfaces 154 of outer drill 104 (FIGS. 1 and 3), whereby lugs 126 will be able to mate with rear support and drive assembly 4 shown in FIG. 1, in the manner disclosed in the above-identified U.S. Pat. No. 4,600,006 (Baker). Alternatively, lugs 126 may be received in other appropriately designed rear support and drive assemblies so that front drill head assembly 100 may be used with such support and drive assemblies.

It is to be appreciated that the foregoing assembly can be achieved only if inner drill 102 and outer drill 104 are properly aligned with one another (i.e., so that the inner drill's flutes 108 are aligned with the outer drill's flutes 160, and so that the inner drill's keys 126 are aligned with the outer drill's slots 156) prior to moving the two drills into engagement. On account of the size and shape of the inner drill's lugs 126 and the size and shape of outer drill 104, if the lugs 126 are not properly aligned with the outer drill's slots 156 when the two drill members are moved together, the end surfaces 130 of the inner drill's keys 126 will encounter the forward surfaces 154 of lips 147 and thereby prevent the inner and outer drills from achieving the position shown in FIG. 3.

In operation, when the cranial perforator is to be used to drill a hole in a skull, the front drill head assembly 100 is mounted to an appropriate rear support and drive assembly (e.g. such as the rear support and drive assembly 4 shown in FIG. 1), and then a powered drive unit (not shown) is used to drive the cranial perforator in a counterclockwise direction. The cranial perforator is brought down so that its pyramidal front projection 118 contacts the skull precisely where the cranial hole is to be made. As the sharp pyramidal projection 118 keeps the cranial perforator centered, the perforator is pressed down against the skull. As the inner drill rotates, its pyramidal projection 118 and its flutes 108 bore into the skul the same time, the outer drill's surfaces 159C are engaged by the rotating lugs' surfaces 134, causing the outer drill to rotate in unison with the inner drill. As seen in FIG. 8, the novel design of front drill head assembly 100 will cause the leading edges of outer drill 104 to engage the skull at the same time that the peripheral edges of the inner drill's flutes 108 engage the skull. Accordingly, outer drill 104 is effectively in engagement with the skull as soon as inner drill 102 is in engagement with the skull. As the perforator cuts its way into the skull, the inner drill's flutes 108 cut a bore, and the outer drill's flutes 160 cut a countersink, so that a bore-countersink opening is formed in the skull. Because the outer drill's front end surfaces 168 and 169 are cut (in the circumferential direction) at a shallower angle than the inner drill's front end surfaces 116, the outer drill will tend to encounter a greater cutting resistance than the inner drill. This feature is critical in order for the cranial perforator's "safety construction" to function properly, as described in U.S. Pat. No. 4,600,006 (Baker).

When the leading edges of the inner drill pass through the target bone, so that it no longer meets a resistive surface and is free to slip forward, the camming action of the outer drill's bevelled surfaces 159C bearing against the inner drill's lug surfaces 134 causes the inner drill to slip forward relative to the outer drill and the rear support and drive assembly far enough for lugs 126 to move out of engagement with the rear support and drive assembly, as described in U.S. Pat. No. 4,600,006 (Baker). With the inner drill no longer coupled to the rear support and drive unit 4, residual friction with the skull causes the rotation of drills 102 and 104 to cease. Further forward penetration of the cranial perforator is impeded at this point, inasmuch as the bore-countersink opening made by the cranial perforator has formed a frustoconical shoulder of bone which blocks forward movement of the front surfaces 168 of the now-stationary outer drill. The cranial perforator may then be removed from the cranial opening simply by pulling it backwards.

Because the inner and outer drills are formed so that the leading portions of the outer drill's front cutting surfaces 169 are contiguous with the peripheral portions of the inner drill's leading surfaces 116 (see FIG. 8), very thin bone can be drilled without the fear that the inner drill will pass all the way through the bone before the outer drill engages the bone. Also, because the inner and outer drills are adapted to cut in a bore-countersink arrangement, a sufficient shoulder of bone will always be provided which is sufficient to impede forward progress of the perforator once the inner and outer drills have been disengaged from the rear support and drive assembly. Thus, operation of the cranial perforator's "safety construction" is assured even with relatively thin skulls.

It is to be appreciated that certain changes may be made to the front drill head assembly 100 without departing from the scope of the present invention.

Figure 9:
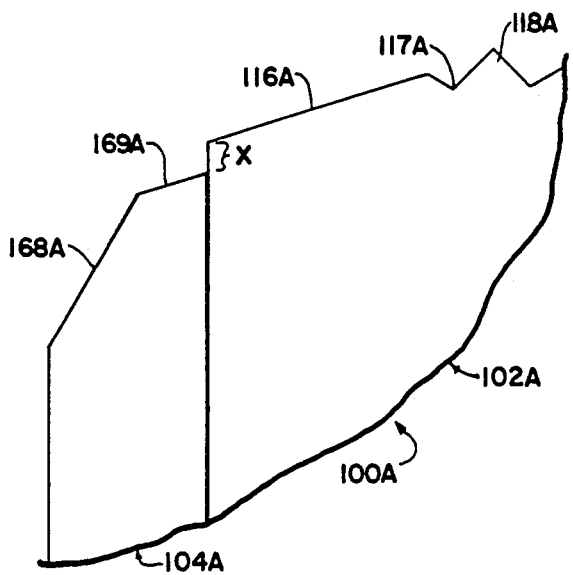
FIG. 9 is an enlarged partial side elevation of a drill head assembly comprising a second embodiment of the present invention.

Thus, for example, an alternative front drill head assembly 100A is disclosed in FIG. 9. Drill head assembly 100A is identical to the foregoing drill head assembly 100, except that the leading portions of the outer drill's surfaces 169A are withdrawn slightly (by a distance denoted by X) from the peripheral portions of the inner drill's surfaces 116A. Since in practice skull thicknesses down to a thickness of about 40/1000 inch have been encountered, the distance X should be something less than 40/1000 inch in length in order to allow front drill head assembly 100A to function in the manner previously described. Preferably, the distance X is 35/1000 inch in length. In this respect, it should be appreciated that with prior art cranial perforators such as that shown in FIG. 1, the leading surfaces of the outer drill are typically displaced approximately 00/1000 inch behind the peripheral surface of the inner drill.

Figure 10:
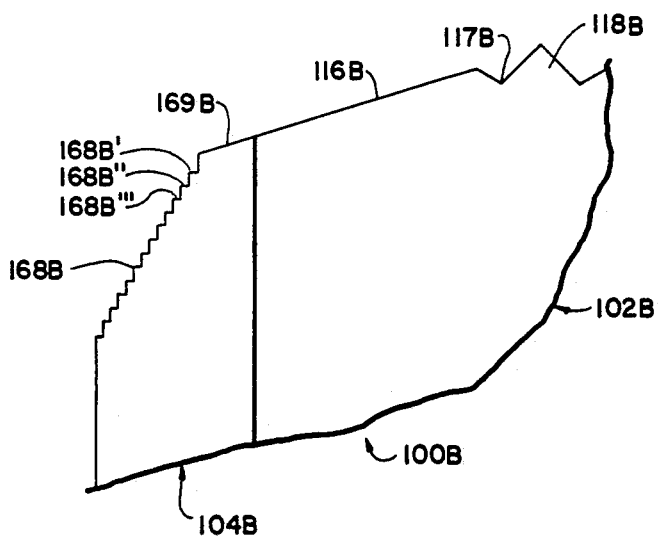
FIG. 10 is an enlarged partial side elevation of a drill head assembly comprising a third embodiment of the present invention.

Looking next at FIG. 10, there is shown an alternative front drill head assembly 100B. Drill head assembly 100B is identical to the foregoing front drill head assembly 100, except that each surface 168 is replaced with a stepped surface 168B comprising steps 168B', 168B", 168'", etc. Stepped surfaces 168B function in the same manner as surfaces 168 previously described, except that by forming surfaces 168B as a series of steps, a bone shoulder of superior thickness and strength is provided.

Figure 11:
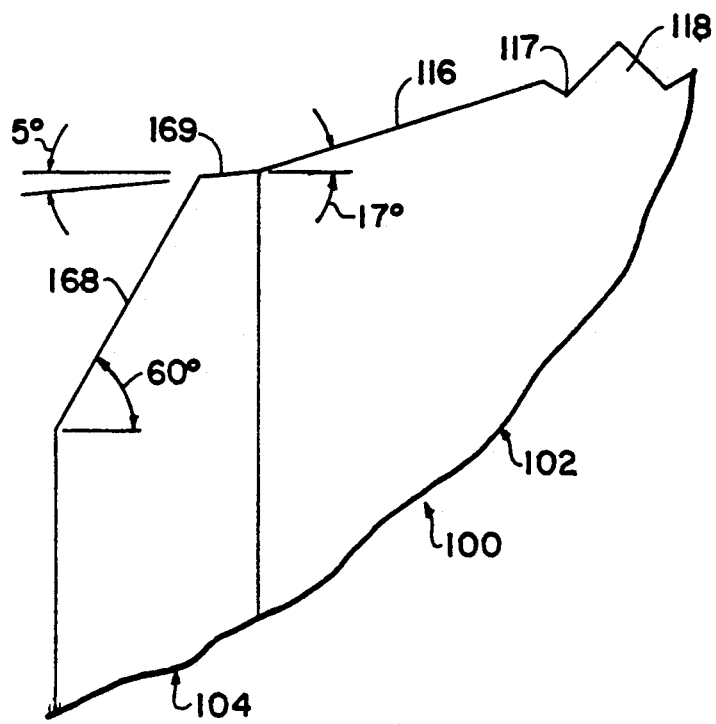
FIG. 11 is an enlarged partial side elevation of a drill head assembly comprising a fourth embodiment of the present invention.

It is also to be appreciated that while in FIG. 8 the outer drill's surfaces 169 are shown to be sloped in the radial direction with the same 17 degree slope as the inner drill's surfaces 116, surfaces 169 could be sloped in the radial direction with a different degree of slope, e.g. 5 degrees as illustrated in FIG. 11. Furthermore, while in FIG. 8 the outer drill's surfaces 168 are shown at a αdegree angle to a plane that intersects the axis of the drill head assembly at a right angle, surfaces 168 could be sloped so as to extend at a different angle to a plane that intersects the axis of the drill head assembly at a right angle, e.g. 45 degrees.

Still other changes of this type will be obvious to persons skilled in the art.

What is claimed is:

1. A perforator comprising:
   (1) a drill head assembly comprising (a) an inner drill having a plurality of inner cutting flutes, each terminating in a front cutting edge, and (b) an outer drill comprising a plurality of outer cutting flutes, each terminating in a front cutting edge, said drill head assembly being constructed so that the leading portions of said front cutting edges of said outer cutting flutes are contiguous with the peripheral portions of said front cutting edges of said inner cutting flutes so long as said drill assembly is enabled and said inner drill encounters a resistive surface; and
   (2) drive means for enabling said drill head assembly when said inner drill is encountering a resistive surface, and disabling said drill head assembly when said inner drill is no longer encountering said resistive surface while said outer drill is still encountering said resistive surface.

2. A perforator according to claim 1 wherein said inner and outer drills each have three flutes.

3. A perforator according to claim 1 wherein said front cutting edges of said outer cutting flutes and said front cutting edges of said inner cutting flutes extend at the same angle to the axis of rotation of said drive means.

4. A perforator according to claim 3 wherein said front cutting edges of said outer cutting flutes and said front cutting edges of said inner cutting flutes extend at an angle of 17 degrees relative to a plane intersecting and extending perpendicular to the axis of rotation of said drive means.

5. A perforator according to claim 3, wherein said front cutting edges of said outer cutting flutes and said front cutting edges of said inner cutting flutes lie along a common plane so long as said drill head assembly is enabled and said inner drill encounters a resistive surface.

6. A perforator according to claim 1 wherein said front cutting edges of said inner cutting flutes extend at a different angle to the axis of rotation of said drive means than the front cutting edges of said outer cutting flutes.

7. A perforator according to claim 1 wherein said front cutting edges of said outer cutting flutes comprise first cutting edges contiguous with said front cutting edges of said inner cutting flutes, and second cutting edges contiguous to said first cutting edges of said outer cutting flutes, and further wherein said first and second cutting edges of said outer cutting flutes are disposed at different angles to the axis of rotation of said drive means.

8. A perforator comprising:
 (1) a drill head assembly comprising (a) an inner drill having a plurality of inner cutting flutes, each terminating in a front cutting edge, and (b) an outer drill comprising a plurality of outer cutting flutes, each having (i) a front cutting edge, and (ii) a side cutting edge, wherein each of said front cutting edges of said outer cutting flutes comprises (a) a first cutting edge adjacent to a corresponding respective one of said front cutting edges of said inner cutting flutes and (b) a second cutting edge contiguous to said first cutting edge and contiguous to a corresponding respective one of said side cutting edges, and further wherein said first cutting edge is inclined at about a 5°–17° angle relative to a plane intersecting and extending perpendicular to the axis of rotation of said outer drill and said second cutting edge is inclined at about a 45°–60° angle relative to said plane, said drill head assembly being constructed so that the leading portions of said first cutting edges of said front cutting edges of said outer cutting flutes are adjacent to and axially displaced a predetermined distance along the axis of said drill head assembly from the peripheral portions of said front cutting edges of said inner cutting flutes so long as said drill head assembly is enabled and said inner drill encounters a resistive surface; and
 (2) drive means for enabling said drill head assembly when said inner drill is encountering a resistive surface, and disabling said drill head assembly when said inner drill is no longer encountering said resistive surface while said outer drill is still encountering said resistive surface.

9. A perforator according to claim 7 wherein said second cutting edges have a terraced configuration.

10. A perforator according to claim 9 wherein said second cutting edges have a terraced configuration.

11. A cranial perforator comprising:
 inner drill means for boring a hole through a skull, said inner drill means comprising a plurality of front cutting edges;
 outer drill means for forming a counterbore in said skull, said outer drill comprising a plurality of front cutting edges;
 drive means for enabling said drill head assembly when said inner drill is encountering a resistive surface, and for disabling said drill head assembly when said inner drill is no longer encountering said resistive surface while said outer drill is still encountering said resistive surface; and
wherein said inner and outer drill means and said drive means are constructed so that each of said plurality of front cutting edges of said inner drill means is contiguous with and extends along the same plane as a corresponding respective one of said plurality of front cutting edges of said outer drill means so long as said drive means is enabled and said inner drill means engages but has not yet bored a hole through said skull.

12. A cranial perforator comprising:
 an inner drill for forming a bore which extends through a skull having an inner surface and an outer surface, said inner drill comprising a plurality of front cutting edges, each of which extends along an axis that forms a predetermined angle with the rotational axis of said inner drill;
 an outer drill comprising:
 first countersink means for forming a first countersink in said skull which (a) is concentric with said bore and (b) has a radially-innermost portion which is axially spaced a predetermined distance from said inner surface of said skull when said bore extends through said skull, wherein said first countersink means comprises a plurality of first front cutting edges, each of which extends parallel to, and is axially spaced about 35/1000 inch from, a corresponding respective one of said front cutting edges of said inner drill;
 second countersink means for forming a second countersink in said skull which (a) is concentric with said bore and (b) intersects the radially-outermost portion of said first countersink; and
 drive means for enabling said inner drill and said outer drill when said inner drill is forming said bore in said skull, and for disabling said inner drill and said outer drill substantially at the instant said inner drill penetrates said inner surface of said skull.

13. A cranial perforator according to claim 12 wherein:
 said first countersink means is designed to form said first countersink so that the walls of said first countersink are inclined at about a 5°–17° angle to a plane intersecting and extending perpendicular to the rotational axis of said outer drill.

14. A cranial perforator according to claim 13 wherein said second countersink means is adapted to form said second countersink so that the walls of said second countersink are inclined at about a 45°–60° angle to a plane extending perpendicular to said rotational axis of said outer drill.

15. A cranial perforator according to claim 12 wherein said first countersink means comprises a plurality of first front cutting edges, each of which edges are inclined at about a 5°–17° angle with respect to a plane extending perpendicular to the rotational axis of said outer drill.

16. A cranial perforator according to claim 15 wherein said second countersink means comprises a plurality of second front cutting edges, each of which intersects a corresponding relative one of said plurality of first front cutting edges on said first countersink means.

17. A cranial perforator according to claim 12 wherein said second countersink means comprises a plurality of second front cutting edges, each of which intersects a corresponding respective one of said first front cutting edges of said first countersink means.

18. A cranial perforator comprising:

an inner drill for forming a bore which extends through a skull having an inner surface and an outer surface;

an outer drill comprising:

first countersink means for forming a first countersink in said skull which (a) is concentric with said bore and (b) has a radially-innermost portion which is axially spaced a predetermined distance from said inner surface of said skull when said bore extends through said skull, wherein said predetermined distance is equal to about 35/1000 of an inch;

second countersink means for forming a second countersink in said skull which (a) is concentric with said bore and (b) intersects the radially-outermost portion of said first countersink; and drive means for enabling said inner drill and said outer drill when said inner drill is forming said bore in said skull, and for disabling said inner drill and said outer drill substantially at the instant said inner drill penetrates said inner surface of said skull.

19. A cranial perforator comprising:

(a) an inner drill for forming a bore which extends through a skull having an inner surface and an outer surface;

(b) first countersink means for forming a first annular sidewall in said skull defining a first frustum which is concentric with said bore, said first sidewall being inclined at about a 5°-17° angle with respect to a plane intersecting and extending perpendicular to the rotational axis of said outer drill, wherein the radially-innermost portion of said first sidewall is axially spaced about 35/1000 of an inch from said inner surface of said skull when said bore extends through said skull;

(c) second countersink means for forming a second annular sidewall in said skull defining a second frustum which is concentric with said bore, said second sidewall being inclined at about a 45°-60° angle with respect to said plane, wherein the radially-innermost portion of said second sidewall intersects the radially-outermost portion of said first sidewall; and (d) drive means for enabling said inner drill and said first and second countersink means when said inner drill is forming said bore in said skull and for disabling said first drill and said first and second countersink means when said inner drill penetrates said inner surface of said skull.

20. A perforator comprising:

(1) a drill head assembly comprising (a) an inner drill having a plurality of inner cutting flutes, each terminating in a front cutting edge, and (b) an outer drill comprising a plurality of outer cutting flutes, each terminating in a front cutting region comprising a first surface having a first cutting edge and a second surface having a second cutting edge, said first cutting edge being inclined at about a 5°-17° angle with respect to a plane intersecting and extending perpendicular to the rotational axis of said outer drill and said second cutting edge being inclined at about a 45°-60° angle relative to said plane, said first surface being contiguous with said second surface, each of said outer cutting flutes additionally comprising a side surface having a side-cutting edge, said side surface being contiguous with said second surface, and further wherein said first and second cutting edges of said front cutting region are disposed at different angles to the rotational axis of the outer drill; and (2) drive means for enabling said drill head assembly when said front cutting edges of said inner drill are encountering a resistive surface, and for disabling said drill head assembly when said front cutting edges of said inner drill are no longer encountering said resistive surface while said first and second cutting edges of said outer drill are still encountering said resistive surface.

21. A perforator according to claim 20 wherein said first surface of said front cutting region is positioned radially inward of said second surface.

22. A perforator according to claim 20 wherein said first and second surfaces of said front cutting region are substantially planar.

23. A cranial perforator according to claim 20 wherein:

said first surface additionally comprises a radially innermost edge, a radially outermost edge, and a trailing edge extending between said innermost edge and said outermost edge; and said second surface additionally comprises a radially innermost edge which is coextensive with said radially outermost edge of said first surface, a radially outermost edge, and a trailing edge extending between said innermost edge and said outermost edge.

24. A cranial perforator according to claim 20 wherein said side cutting edge is contiguous with said second cutting edge.

* * * * *

UNITED STATES PATENT AND TRADEMARK OFFICE
CERTIFICATE OF CORRECTION

PATENT NO. : 5,007,911
DATED : April 16, 1991
INVENTOR(S) : John W. Baker It is certified that error appears in the above-identified patent and that said Letters Patent is hereby corrected as shown below:

Claim 16, col. 10, line 60, the word "relative" should be changed to the word -- respective --.

Signed and Sealed this

Twentieth Day of October, 1992

*Attest:*

DOUGLAS B. COMER

*Attesting Officer*      *Acting Commissioner of Patents and Trademarks*